US012708342B2

(12) United States Patent
Brueck et al.

(10) Patent No.: US 12,708,342 B2
(45) Date of Patent: Aug. 18, 2026

(54) RADIOLOGY WORKFLOW

(71) Applicant: KONINKLIJKE PHILIPS N.V., Eindhoven (NL)

(72) Inventors: Heiner Matthias Brueck, Pinneberg (DE); Sven Kroenke-Hille, Hamburg (DE); Jens Von Berg, Hamburg (DE); Daniel Bystrov, Hamburg (DE); Andre Gooben, Eldena (DE); Stewart Matthew Young, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 143 days.

(21) Appl. No.: 18/851,183

(22) PCT Filed: Mar. 16, 2023

(86) PCT No.: PCT/EP2023/056689
§ 371 (c)(1),
(2) Date: Sep. 26, 2024

(87) PCT Pub. No.: WO2023/186551
PCT Pub. Date: Oct. 5, 2023

(65) Prior Publication Data

US 2025/0169789 A1 May 29, 2025

(30) Foreign Application Priority Data

Mar. 31, 2022 (EP) .................................... 22166066

(51) Int. Cl.
*A61B 6/00* (2024.01)
*A61B 6/58* (2024.01)
(Continued)

(52) U.S. Cl.
CPC ................ *A61B 6/566* (2013.01); *A61B 6/00* (2013.01); *A61B 6/587* (2013.01); *G16H 30/20* (2018.01);
(Continued)

(58) Field of Classification Search
CPC .. A61B 6/00; A61B 6/08; A61B 6/566; A61B 6/587; A61B 6/588; A61B 6/589;
(Continued)

(56) References Cited

U.S. PATENT DOCUMENTS

2011/0010192 A1 1/2011 Backhaus
2015/0180917 A1 6/2015 Im
(Continued)

FOREIGN PATENT DOCUMENTS

CN 103239256 A 8/2013
TW 202101400 A 1/2021
(Continued)

OTHER PUBLICATIONS

PCT International Search Report, International application No. PCT/EP2023/056689, May 16, 2023.
(Continued)

*Primary Examiner* — Mark R Gaworecki
(74) *Attorney, Agent, or Firm* — Larry Liberchuk

(57) ABSTRACT

Many potential interactions may occur during the planning and execution of non-standard projections in radiological examinations, leading to an increased risk of error and a longer, more complex, and costly workflow. There is provided a method to be used in radiology workflow which comprises, in a planning step, enabling a first user to prepare an imaging examination request defining a non-standard projection for a radiographic image; in a communication step, processing the imaging examination request to generate positional instructions on how to achieve the non-
(Continued)

standard projection, outputting the positional instructions to a second user, and receiving a radiographic image acquired using the non-standard projection; and, in a verification step, determining whether the received radiographic image fulfils the imaging examination request. The method thus facilitates the planning and execution of the acquisition of a radiographic image using a non-standard projection, while reducing the risk, complexity, duration and cost of the workflow.

15 Claims, 6 Drawing Sheets

(51) Int. Cl.

| | |
|---|---|
| ***G16H 30/20*** | (2018.01) |
| ***G16H 30/40*** | (2018.01) |
| ***G16H 80/00*** | (2018.01) |
| *A61B 6/08* | (2006.01) |
| *G16H 50/20* | (2018.01) |

(52) U.S. Cl.
CPC ............ *G16H 30/40* (2018.01); *G16H 80/00* (2018.01); *A61B 6/08* (2013.01); *A61B 6/588* (2013.01); *A61B 6/589* (2013.01); *G16H 50/20* (2018.01)

(58) Field of Classification Search
CPC ........ G16H 30/20; G16H 30/40; G16H 50/20; G16H 80/00
See application file for complete search history.

(56) References Cited

U.S. PATENT DOCUMENTS

| | | | | |
|---|---|---|---|---|
| 2016/0220844 | A1* | 8/2016 | Paysan | G16H 10/60 |
| 2019/0117190 | A1 | 4/2019 | Djajadiningrat | |
| 2019/0183438 | A1* | 6/2019 | Joerger | A61B 6/469 |
| 2023/0027305 | A1* | 1/2023 | Foos | G16H 50/20 |
| 2023/0404495 | A1 | 12/2023 | Brueck | |

FOREIGN PATENT DOCUMENTS

| | | | |
|---|---|---|---|
| WO | WO2020115307 | A1 | 6/2020 |
| WO | WO2023020865 | A1 | 2/2023 |
| WO | WO2023031001 | A1 | 3/2023 |

OTHER PUBLICATIONS

Martinez A. et al., "XAP-Lab: A Software Tool for Designing Flexible X-Ray Acquisition Protocols", Computer Methods and Programs in Biomedicine, vol. 177, pp. 243-252, 2019.

M. Brück et al. "Robust Quality Assessment for Skeletal Radiographs: Combining Convolutional Neural Networks and Statistical Atlases". Online Conference to Unite Philips AI (OCUPAI), May 2020.

Krönke S. et al., CNN-Based Pose Estimation of Musculoskeletal X-Ray Images, Online Conference to Unite Philips AI (OCUPAI), Jun. 2021.

Krönke S. et al., CNN-Based Pose Estimation for Assessing Quality of Ankle-Joint X-Ray Images, SPIE Medical Imaging Conference, vol. 12032, 2022.

Mairhöfer D. et al., "An AI-Based Framework for Diagnostic Quality Assessment of Ankle Radiographs", (PMLR) Proceedings of the Fourth Conference on Medical Imaging with Deep Learning (MIDL), No. 143, pp. 484-496, Jul. 2021.

* cited by examiner

RADIOLOGY WORKFLOW

FIELD OF THE INVENTION

The invention relates to methods and systems to be used in radiology workflow.

BACKGROUND OF THE INVENTION

FIG. 1 illustrates a typical workflow 100 for a radiographic imaging examination, which begins with the referring physician requesting an X-ray image from the radiology department. Standard projections exist for all parts of the human anatomy, which are well documented. However, patient conditions sometimes call for projections that do not conform to these standards. The referring physician may indicate to the radiographer how they should deviate from the closest standard projection (e.g., for an X-ray of an ankle, "AP mortise plus 10 degrees medial rotation") in the request. However, such deviations can be difficult to describe clearly due to the number of degrees of freedom involved. The referring physician may therefore supervise the radiographer or even perform the patient positioning themselves. FIG. 1 further illustrates the many potential interactions and consultations which may occur during the planning and execution of non-standard projections, particularly in case of the need for clarification, leading to an increased risk of error and a longer, more complex, and costly workflow.

SUMMARY OF THE INVENTION

It would be desirable to provide a technical solution to one or more of the above-mentioned problems. There is therefore provided, in a first aspect of invention, a method to be used in radiology workflow. The method may comprise, in a planning step, enabling a first user to prepare an imaging examination request defining a non-standard projection for a radiographic image. The method may comprise, in a communication step, processing the imaging examination request to generate positional instructions on how to achieve the non-standard projection, outputting the positional instructions to a second user, and receiving a radiographic image acquired using the non-standard projection. The method may comprise, in a verification step, determining whether the received radiographic image fulfils the imaging examination request.

The method thus facilitates the planning and execution of the acquisition of a radiographic image using a non-standard projection, while reducing the risk, complexity, duration and cost of the workflow. The method may provide further benefits when combined with patient positioning support technology (e.g. using 3D camera systems) in making the acquisition of images with non-standard projections as straightforward as those with standard projections. The method may be performed by a planning tool as described herein, which may also be described as an interactive 3D planning tool, or a virtual X-ray planning tool for non-standard X-ray projections.

As mentioned above, the imaging examination request defines the non-standard projection for the radiographic image. The imaging examination request may be referred to simply as an exam request. To define the non-standard projection, the exam request may specify values for one or more patient position parameters relative to the projection geometry. Parameters of the projection may be stipulated in a way which facilitates both acquisition and verification of the radiographic image. Parameters may be specified alongside particular acceptance criteria to allow a determination to made as to whether the acquired image passes the verification, as described elsewhere herein. The exam request may specify a detector configuration, comprising a position and/or orientation of the detector. The exam request may specify a source configuration, comprising a position and/or orientation of the source. The exam request may specify an anatomy configuration, comprising a position and/or orientation of at least one part of the anatomy to be imaged. Where that includes a joint, the anatomy configuration may specify one or more articulation angles of the joint. The exam request may specify a beam configuration, comprising a position and/or orientation of the beam emanating from detector. The exam request may specify a collimator configuration, indicating one or more collimation parameters. The exam request may specify a region of intersection between the beam and the anatomy. In any of these ways, a formal description of the acquisition may form an integral part of the imaging examination request.

By "non-standard" projection is meant that the projection deviates in at least one respect from at least one standard projection, or more particularly from each member of a set of standard projections. A projection may also be referred to as a view. The set of standard projections may be defined by a radiological handbook or standard. One example of a handbook defining an exemplary set of standard projections is KATHY MCQUILLEN-MARTENSEN. Radiographic Image Analysis. 5th Edition—Apr. 18, 2018. ISBN: 9780323522816. Chapter I. A further exemplary, non-exhaustive set of standard projections for the ankle joint includes AP (anteroposterior), PA (posteroanterior), DP (dorsal-plantar), lateral (taken with the central ray perpendicular to the midsagittal plane), oblique (taken with the central ray at an angle to any of the body planes), flexion (a joint is imaged while in flexion), extension (a joint is imaged while in extension), prone (with the patient lying on their front), supine (with the patient lying on the back), cranial or cephalad (tube angulation towards the head), caudal (tube angulation towards the feet). Yet further examples of standard projections may be specified by or for particular users such as radiology departments, for example an internal standard projection such as "Prof.xxx-view".

The first user preparing the imaging examination request may be any user involved in planning the image acquisition, for example the referring physician. The second user receiving the positional instructions may be any user involved in acquiring the radiographic image, for example a radiographer, a radiologist, or a radiology department, for example.

It will be understood that the patient may human or animal.

The method may enable the imaging examination request to be prepared, including definition of the non-standard projection for a radiographic image, by means of presenting a user interface. The user interface may enable values of parameters of the non-standard projection to be input. The user interface may present a 3D model of the anatomy to be imaged. The 3D model of the anatomy may be specific to a particular patient, e.g., the patient to be imaged, or may be a generic model. The 3D model may enable pose manipulations for one or more of the anatomy of interest, detector, source, and collimator. The 3D model may comprise a joint model. In this case, the joint model can be articulated to enable an indication of the flexion of the joint to be specified. The user interface may indicate the non-standard projection, for example by indicating the direction or position and/or orientation of the non-standard projection relative to the 3D model of the anatomy. Similarly, the user interface may indicate one or more standard projections for reference. The user interface may indicate the position and/or orientation of the non-standard projection relative to one or more standard projections. Projections, whether standard or non-standard, may be indicated by means of a line, arrow, or beam, for example the central beam emanating from the source. The user interface may enable a synthetic preview radiographic image to be generated and shown. The preview image may be generated using the model and optionally also one or more physical assumptions. The preview image may show image features, for example contour highlighting (e.g., bone contours) and/or selected exemplary anatomical landmarks. These landmarks might for example correspond to locations that can be easily palpated by the radiographer (e.g. lateral malleolus). The proposed visualization thus supports the radiographer in gaining the necessary 3D understanding of the bony geometry more quickly. The projected contours and/or landmarks may be generated using projective geometry. Different views of the model may be available via the user interface for display individually or simultaneously. The views may comprise 2D projections in common anatomical planes, e.g., a top view, side view, front view, and so on. The user interface may facilitate user interaction, enabling one or more interaction options such as rotate, drag, zoom of the virtual setup in 3D. The articulated 3D model may be built from MR or CT scans that capture a range of articulation states. Special models may be generated for gender or age.

The method may further comprise ascertaining whether the requested non-standard projection is feasible in view of constraints imposed by a target imaging system. The imaging system may also be referred to as an image acquisition unit or the like. To this end, data defining such constraints for one or more imaging systems may be used. Exemplary constraints may relate to the mobility of one or more components of the imaging system, for example the source and/or detector. Such constraints may relate to degrees of freedom, range of motion, and/or dimensions of such components. Such constraints may be integrated into the 3D model to be expressed as limitations on the user's ability to reposition the imaging system using the user interface.

The method may comprise checking the desirability of the requested patient position. For example, guidelines defining patient positions or ranges of positions may be available for a given exam type and classified according to their desirability, for example as acceptable, preferable, or optimal. These guidelines may be provided by members of the radiology department or other experts. The guidelines may be intended to avoid injury, pain, or discomfort in the patient. The method may comprise checking patient positioning dynamically during user manipulation of the 3D model and indicating the desirability of the patient positioning. Similarly, the method may comprise seeking and obtaining manual confirmation of the requested patient positioning, for example from the radiographer or radiologist, before completion of the planning step. The method may comprise storing such user input in the guidelines to be applied in future image planning. Such guidelines may be used in conjunction with algorithms (such as SmartOrtho) which automatically assess the positioning quality of radiographic images. The method may comprise using the user interface as described herein to define acceptable, preferable, or optimal patient positioning for given exam types.

Once a non-standard projection has been defined using the user interface, this may be saved for future reuse (e.g., in the case of re-examinations), for example in the medical record of the patient in question.

The positional instructions enabling the second user to achieve the non-standard projection may comprise one or more patient positioning instructions. The patient positioning instructions may comprise instructions on patient orientation, e.g., whether the patient is to lie on their front, back, or left or right side (supine, prone, etc.). The patient positioning instructions may comprise instructions or recommendations on the use of positional support material (e.g., foam blocks, head rests, and so on). The positional instructions may comprise equipment positioning instructions. The equipment positioning instructions may comprise instructions on how to set up one or more components of the imaging system, such as the source (e.g., the X-ray tube), the detector, and the collimator. The positional instructions may alternatively be referred to as guidance data.

The positional instructions may comprise graphical instructions. The graphical instructions may illustrate the requested patient positioning, and/or the requested equipment positioning, and/or the requested positioning of the patient relative to the imaging system. The graphical instructions may illustrate one or more reference positions and/or orientations to which the requested position and/or orientation relates. The graphical instructions may illustrate one or more distances and/or angles between a requested position and/or orientation and a reference position and/or orientation. The graphical instructions may comprise schematic representations of the patient (e.g., the anatomy) and/or of the imaging system or its components. The graphical instructions may be animated, for example to indicate how (e.g., in which direction) the patient and/or the imaging system should be moved to achieve the non-standard projection.

The positional instructions may comprise textual and/or audio instructions. Such guidance may be expressed in medical language.

Positional instructions as described herein enable the requested non-standard positioning to be compared with the current real patient positioning, thereby facilitating realization of the (referring physician's) exam request.

The positional instructions may comprise at least one visual representation of a current alignment and/or a target alignment. The visual representation may show an optical path resulting from the alignment (e.g. an arrow). The visual representation of the current alignment and the target alignment may be displayed on the same screen in one window or in separate windows. The visual representation of the current alignment and/or the target alignment may advantageously simplify the adaption process from the current alignment to the target alignment, since the user can watch the differences on the screen. The current alignment may be ascertained using a patient positioning system as known in the art, which may be camera-based. For example, the current alignment may be derived from at least one optical sensor and/or a control signal of the imaging system. The optical sensor may measure one or more positions of the region of interest. Based on the measurements, patient positioning data such as angle, distance etc. are derived. The control signal may indicate a position and/or orientation of one or more components of the imaging system (i.e. source and/or detector). This may be advantageous since every adaption of the alignment is visible and serves for improving the adaption from the current alignment to the target alignment. The visual representation may be updated to reflect the current alignment. This may be advantageous in terms of improvement of the current alignment in order to fit the target alignment. The visual representation may be continuously or periodically updated.

The positional instructions may comprise at least one visual representation of the region of interest. The visual representation may be an average representation of the region of interest (e.g. a joint, such as a knee or ankle joint), which is used for all patients, or a personalized representation of the region of interest based on patient data. The visual representation of the region of interest may advantageously simplify the adaption process from the current alignment to the target alignment since the user can watch on the screen how to adapt the position of the region of interest instead of relying on their imagination. The positional instructions may further comprise a visual representation of the imaging system.

The positional instructions may comprise an absolute value. The absolute value may be for example an angle (e.g., 10° difference between the current alignment and the target alignment) shown in numbers and/or tables. This may be advantageous for the adaption process for a user due to a reduction in complexity.

The positional instructions may further comprise one or more sequence recommendations for adapting patient and/or system positioning to implement the non-standard projection. The sequence recommendation may pertain to the order in which body parts of the patient and/or components of the imaging system are moved or positioned. This may be advantageous since parameters may interact disadvantageously (e.g. when one parameter of the positioning has the target value, that parameter may constrain the adaption of another parameter of the positioning).

The positional instructions may comprise a preview image of the region of interest based on the current alignment. The preview image may comprise a simulated image representing what would be acquired with the current alignment in an actual image acquisition. The simulated image may be derived from the 3D model of the region interest and the current alignment. In other words, based on the current alignment and the 3D model, a calculation algorithm may calculate a forward projection that would be imaged in the case that the current alignment were used in reality. This may be advantageous in terms of balancing whether the current alignment may already be sufficient. In this content, the method is provided, wherein the preview image is preferably updated dependent on the current alignment. This may be advantageous in terms of improving the current alignment. The preview image may be adapted continuously or periodically. This may simplify the preparation process and helps the radiographer in reaching the target alignment. The simulated image representing the projection may be a pseudo X-ray image generated from the 3D model using parallel or projective projection of the 3D model onto a virtual detector plane. This may be advantageous for improving positioning data.

The positional instructions may comprise palpation guidance for the radiographer. The palpation guidance may relate to the palpation of one or more palpable bony landmarks of a patient, e.g., of the region of interest. To this end, the method may comprise obtaining positioning data for one or more anatomical landmarks, such as the one or more palpable bony landmarks. This may be achieved by the radiographer palpating the region of interest with their hands while a positioning system measures the spatial position of the radiographer's fingertips in order to obtain the positioning data for the palpable bony landmarks. Additionally or alternatively, the radiographer may utilize an auxiliary instrument, e.g. a wearable tracking device on the hand, wrist, or finger (e.g. an electromagnetic tracking device or reflective markers for optical tracking) to obtain the positioning data. The positioning data may be tracked continuously or periodically. The positional instructions may then comprise one or more instructions indicating how the palpable bony landmarks are to be moved in order to bring the patient and/or imaging system from their current systems into the target position for realizing the specified non-standard projection.

The term "palpable bony landmark", as used herein, relates to a bony landmark which is normally hidden by tissue and skin of a subject such that the palpable bony landmark cannot be detected directly, i.e. it cannot be seen, by e.g. a visual system (e.g. human eyes or a camera or the like). The palpable bony landmark may be a suitable bone part, bone section, etc., such as an ankle, which might be hidden by too much tissue of an overweight person. Correspondingly, the term palpation, as used herein, relates to a tactile sampling. The palpation may be carried out by a human (e.g. a radiographer) or by a soft tissue robot. Palpation may also be carried out by a human with an auxiliary instrument, such as a pointing device or the like.

The positional instructions may comprise translational instructions, rotational instructions, or both, providing the radiographer with guidance on how to achieve the non-standard projection.

Generating the positional instructions may comprise using one or more generative models. The generative models may be configured to generate the positional instructions using schematic image generation (e.g., in the case of graphical instructions) and/or natural language processing (NLP, e.g., in the case of textual and/or audio instructions). Additionally or alternatively, generating the positional instructions may comprise using a database that links aspects of geometrical specifications of projections to preprepared positional instructions.

The positional instructions may be output to the second user using any appropriate user interface technology, for example display devices and/or audio devices at the imaging site. It will be appreciated that the first and second users are likely not at the same location. The positional instructions may therefore be output as a data file and transmitted from the first user to the second user via their respective computing systems and an interconnecting network, e.g., the internet. The data may be stored in a computer-readable file format which is suitable for such transmission and for ready access by the second user. In one example, the second user may be the radiographer. Positional instructions may furthermore be sent to other users, such as clinical stakeholders in the radiology value chain, for example the radiologist and/or another physician. In other examples, in which the referring physician and radiographer are at the same location, such transmission may not be necessary.

In one example, in the case that a 3D reconstruction (e.g. from a CT or MR scan) exists for a particular patient, outputting the positional instructions may comprise producing (e.g., by 3D printing) a patient-specific casting for surrounding the anatomy of interest, wherein the casting is configured to provide one or more visual indications of the requested projection geometry. For example, the casting may be configured such that a proxy of the central beam (i.e. using the light gate or a laser) aligns with the casting in a predetermined way to indicate the required pose.

The radiographic image comprises in one example an X-ray image but could be an image acquired using any imaging modality in which a particular projection is to be planned and executed. The radiographic image may be stored in any appropriate file format. In one example, the radiographic image takes the form of a DICOM image. Digital Imaging and Communications in Medicine (DICOM) is a standard pertaining to the communication and management of medical imaging information and related data. In the case that the first and second users are at different locations, the radiographic image may be received after transmission to the first user from another user (for example, from the second user, e.g. the radiographer, and/or from a third user, e.g. the radiologist). Such transmission may be direct or indirect, for example by passing through other stakeholders before returning to the first user. The radiographic image may be received as part of a radiological report, as is known in the art. The radiological report may further comprise data indicating deviations from standard projections. Such data may also be communicated to the radiologist to support the interpretation process and/or to other stakeholders in the clinical management process.

In the verification step, determining whether the received radiographic image fulfils the imaging examination request may comprise comparing or cross-referencing the received image with reference data. The reference data may comprise a reference image, e.g. the synthetic preview image generated using the 3D model. Additionally or alternatively, the reference data may comprise non-image data defining the non-standard projection, for example in terms of one or more pose parameters. Comparing the received image with the reference data may comprise determining whether the received image satisfies one or more acceptance criteria, comprising for example one or more ranges, tolerances, constraints, and/or rules, for determining the acceptability of deviations. The acceptance criteria may be specified in the exam request itself or may be stored separately, for example in a model or database.

In one example, determining whether the received radiographic image fulfils the imaging examination request may comprise performing a similarity check. Performing the similarity check may comprise calculating one or more similarity/distance metrics describing the similarity/distance between the received image and a reference image, e.g. the synthetic preview image. Performing the similarity check may comprise comparing one or more features (e.g., bone contours and/or landmarks) of the received image and corresponding features of the reference image, and computing one or more similarity scores (e.g., a contour similarity/distance score and/or a landmark similarity/distance score). To this end, feature detection and/or image segmentation may be performed to identify features for use in the similarity check.

In another example, determining whether the received radiographic image fulfils the imaging examination request may comprise obtaining an AI-based interpretation of the received image, for example using a model of the anatomical joint of interest. For example, a machine learning model may be trained to highlight deviations in the received image.

Determining whether the received radiographic image fulfils the imaging examination request may comprise deriving pose parameters of the projection used in the received image, and comparing the derived pose parameters to requested pose parameters.

Determining whether the received radiographic image fulfils the imaging examination request may comprise performing one or more verification checks. The verification checks may comprise one or more range checks to check that parameter values fall within corresponding minimum-maximum ranges. The verification checks may comprise a constraint check to check that one or more constraints are satisfied. The verification checks may comprise one or more rule-based checks to ensure that the received image is consistent with one or more rules, requirements, or assumptions. The verification checks may comprise a format check to ascertain that the received image conforms to a required format. The verification checks may comprise one or more presence checks for required image content.

Deviations from the requested non-standard projection may be indicated in one example by highlighting mismatched areas in the received image, for example in the case that a machine learning model is used to perform the verification. Additionally or alternatively, the verification may simply output a binary indication of success or failure, for the overall image and/or for individual acceptance criteria. Verification failure may trigger a request or suggestion to perform a retake of the image.

The method of the first aspect may be computer implemented.

According to a second aspect, there is provided a computing system configured to perform the method of the first aspect.

According to a third aspect, there is provided a computer program product comprising instructions which, when executed by a computing system, enable or cause the computing system to perform the method of the first aspect.

According to a fourth aspect, there is provided a computer-readable medium comprising instructions which, when executed by a computing system, enable or cause the computing system to perform the method of the first aspect.

The invention may include one or more aspects, examples or features in isolation or combination whether or not specifically disclosed in that combination or in isolation. Any optional feature or sub-aspect of one of the above aspects applies as appropriate to any of the other aspects.

These and other aspects of the invention will be apparent from and elucidated with reference to the embodiments described hereinafter.

BRIEF DESCRIPTION OF THE DRAWINGS

A detailed description will now be given, by way of example only, with reference to the accompanying drawings, in which:—

DETAILED DESCRIPTION OF EMBODIMENTS

Figure 1:
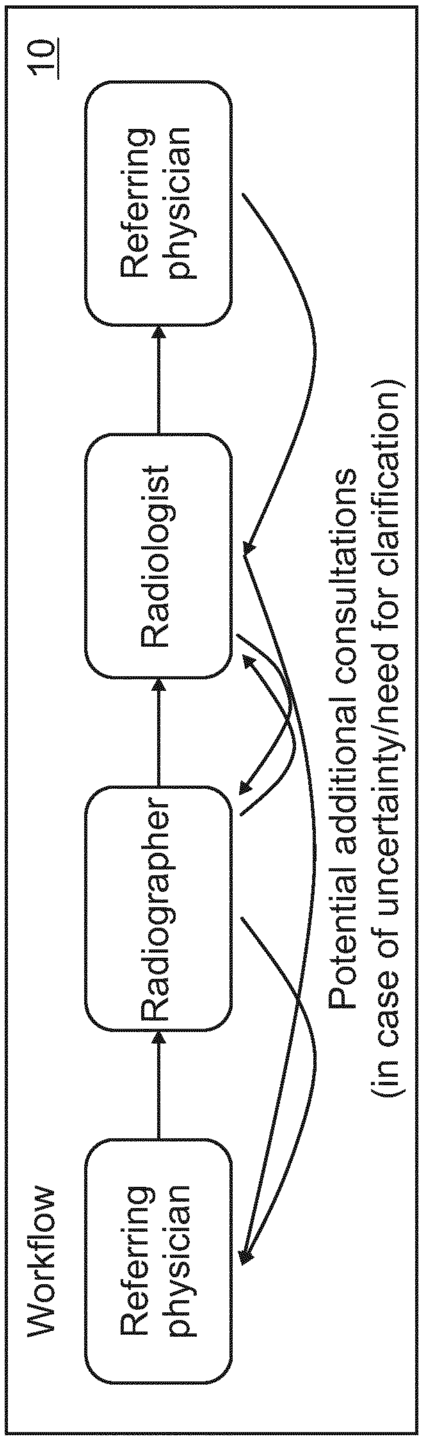
FIG. 1 illustrates a typical workflow for a radiographic imaging examination.
Figure 2:
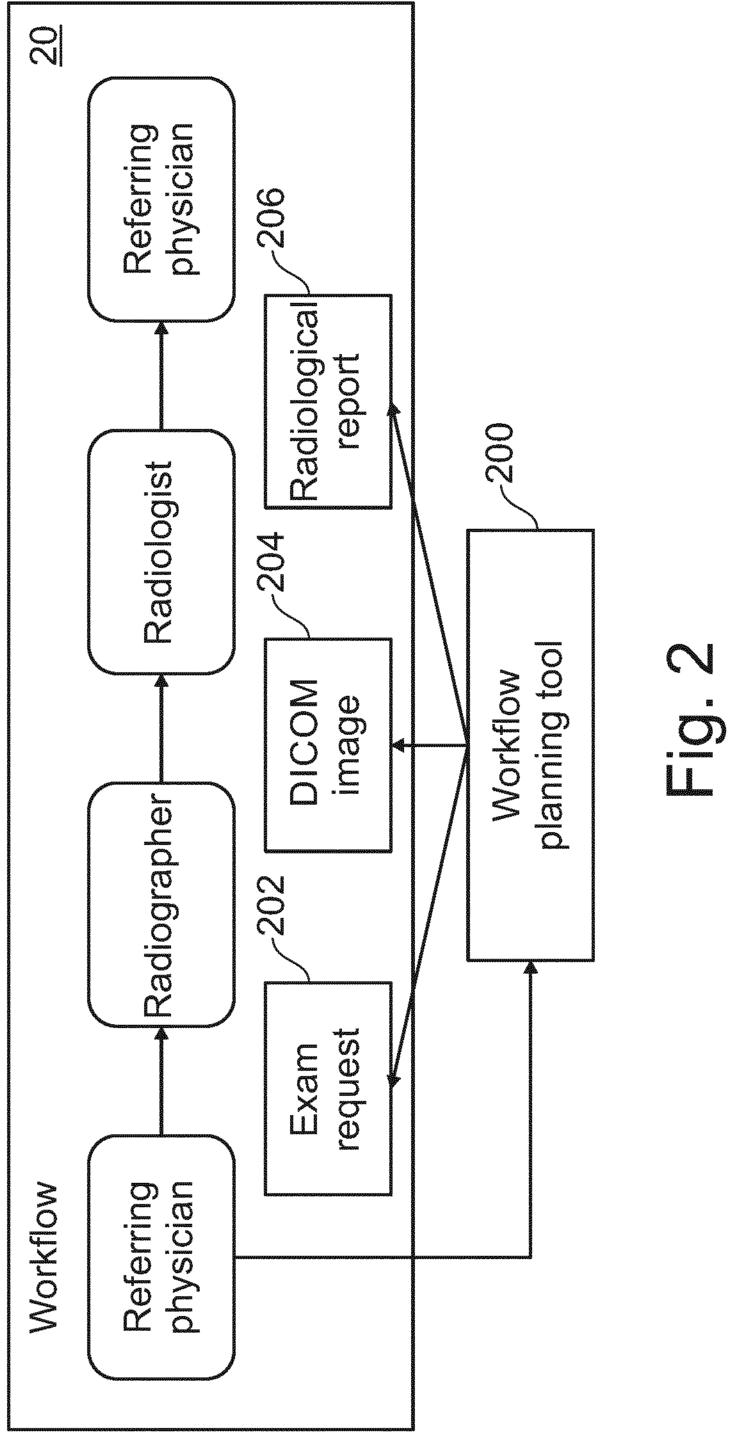
FIG. 2 illustrates an improved workflow for a radiographic imaging examination using a planning tool according to the present disclosure.

FIG. 2 illustrates an improved workflow 20 for a radiographic imaging examination using a planning tool 200 according to the present disclosure. The planning tool 200 may be used to facilitate the planning, acquisition, and verification of a non-standard radiographic image using reduced communication compared to the workflow 10 of FIG. 1.

Using the planning tool 200, the referring physician (e.g. an orthopaedic surgeon) interactively configures a 3D model to indicate a specific non-standard projection of an anatomy to be examined by radiography. The planning tool 200 allows the configuration to be visualized in 3D and simulated to produce a pseudo or synthetic radiographic image. Once finalized, pose parameters are transferred to the radiology department where they can be used to position the patient accordingly. After the acquisition, the planning tool 200 is again used to compare the real radiographic image to the specified non-standard projection to verify that the referring physician's request has been satisfied. This workflow 20 rationalizes the communication between the referring physician and the radiographer through the use of a precise and comprehensive specification. 2D and 3D visualization support, and a verification step. Clear and easy communication becomes even more important when the referring physician and radiographer are physically separated, as with radiology in acquisition centers. The planning tool 200 facilitates the communication along the workflow using artefacts to support information exchange. The artefacts in the non-limiting example shown include one or more of an exam request 202, a DICOM image 204, and a radiological report 206. However, it will be understood that essentially all exam and image data along with related metadata are potential artefacts of interest (including, but not limited to, patient specific data (e.g., age, gender, weight, size, clinical status, pain, disabilities, prothesis, and so on) or technical data (exposure time, kV, and so on). It may be useful that deviations from standard projections are communicated to the radiologist to support the interpretation process. These details may be available in the radiological report to support any further image evaluation by the referring physician or other stakeholders in the clinical management process.

Figure 3:
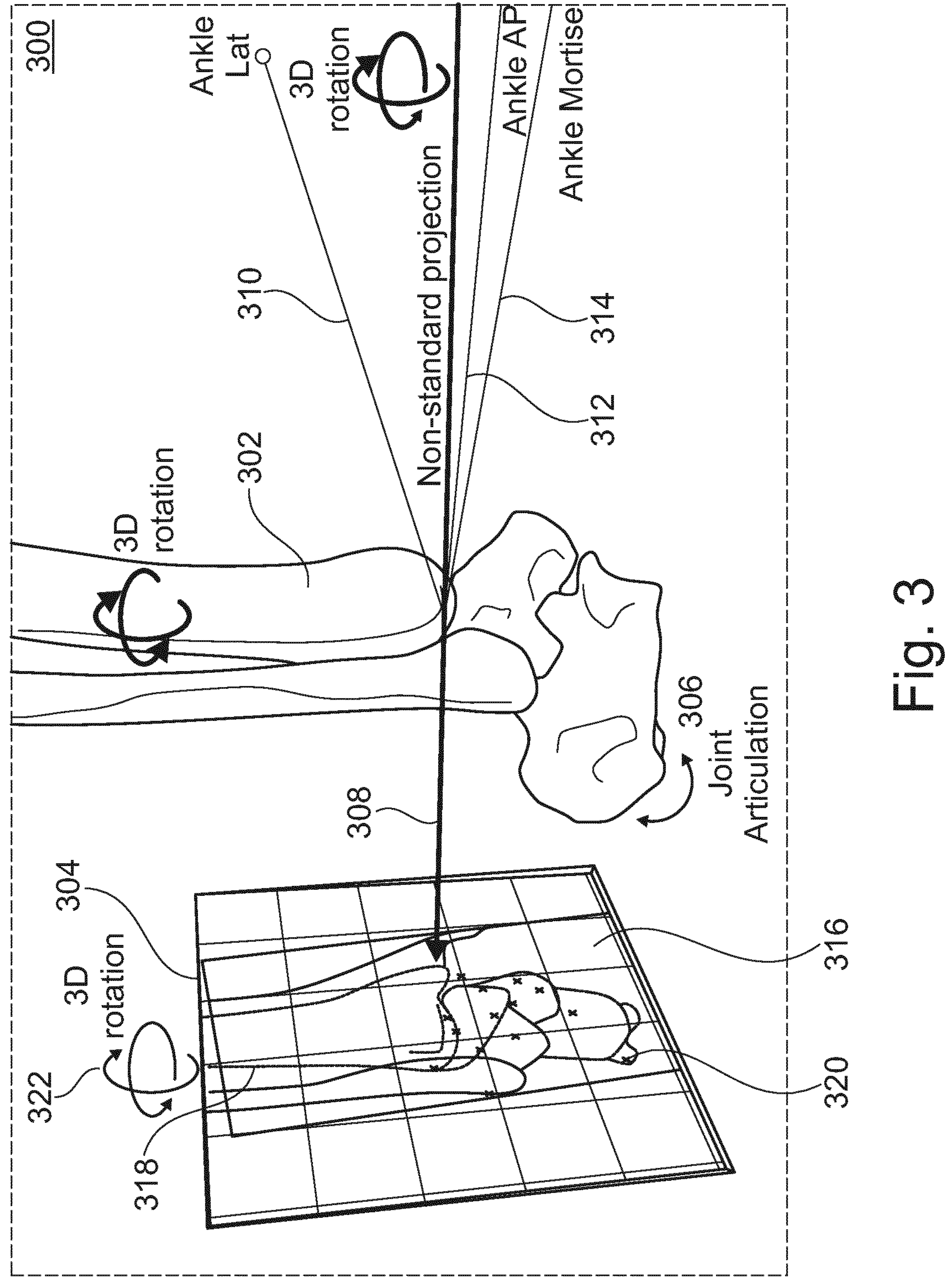
FIG. 3 shows one example of a user interface of the planning tool being used to define a non-standard projection.

FIG. 3 shows one example of a user interface 300 of the planning tool 200 being used to define a non-standard projection. The user interface 300 allows the specification of the patient position relative to the X-ray geometry, for the definition of the non-standard projection. Using the user interface 300, the referring physician can modify various parameters to specify the projection for the radiographer. In particular, 3D pose manipulations are possible using a 3D model of the anatomy of interest 302 (in this non-limiting example, an ankle), detector 304 and source (not shown). The position and direction of the source and detector 304, including the central beam direction and the intersection of the central beam with the anatomy 302, can all be specified.

The user interface 300 also allows the joint articulation 306 to be specified in the 3D model of the anatomy 302. The joint model can be articulated, in this non-limiting example to indicate the flexion of the upper ankle joint. The articulated model that is used by the planning tool 200 can be built from MR or CT scans that capture the range of articulation states. Special models can be generated for gender or age.

The user interface 30 indicates, using the beam 308, (the central beam of) the non-standard projection direction. This may be illustrated alongside and relative to well-established standard projections, which in this non-limiting example comprise Ankle Lat 310, Ankle AP 312, and Ankle Mortise 314.

The user interface 300 displays a synthetic X-ray preview image 316. The synthetic preview image 316 is generated using the 3D model and some physical assumptions, relating for example to the Beer-Lambert law, statistical methods of ray aggregation, and/or assumptions about material properties (e.g., bone density and attenuation). The synthetic preview image in this example shows bone contour highlighting 318 and exemplary anatomical landmarks 320 such as key points of the bones. These landmarks might for example correspond to locations that can be easily palpated by the radiographer (e.g. lateral malleolus). The generation of projected contours or landmarks is achieved using projective geometry.

The user interface 300 includes various elements, such as that shown at 322, providing the user with the option to rotate, articulate, drag, or zoom the virtual setup in 3D.

Figure 4:
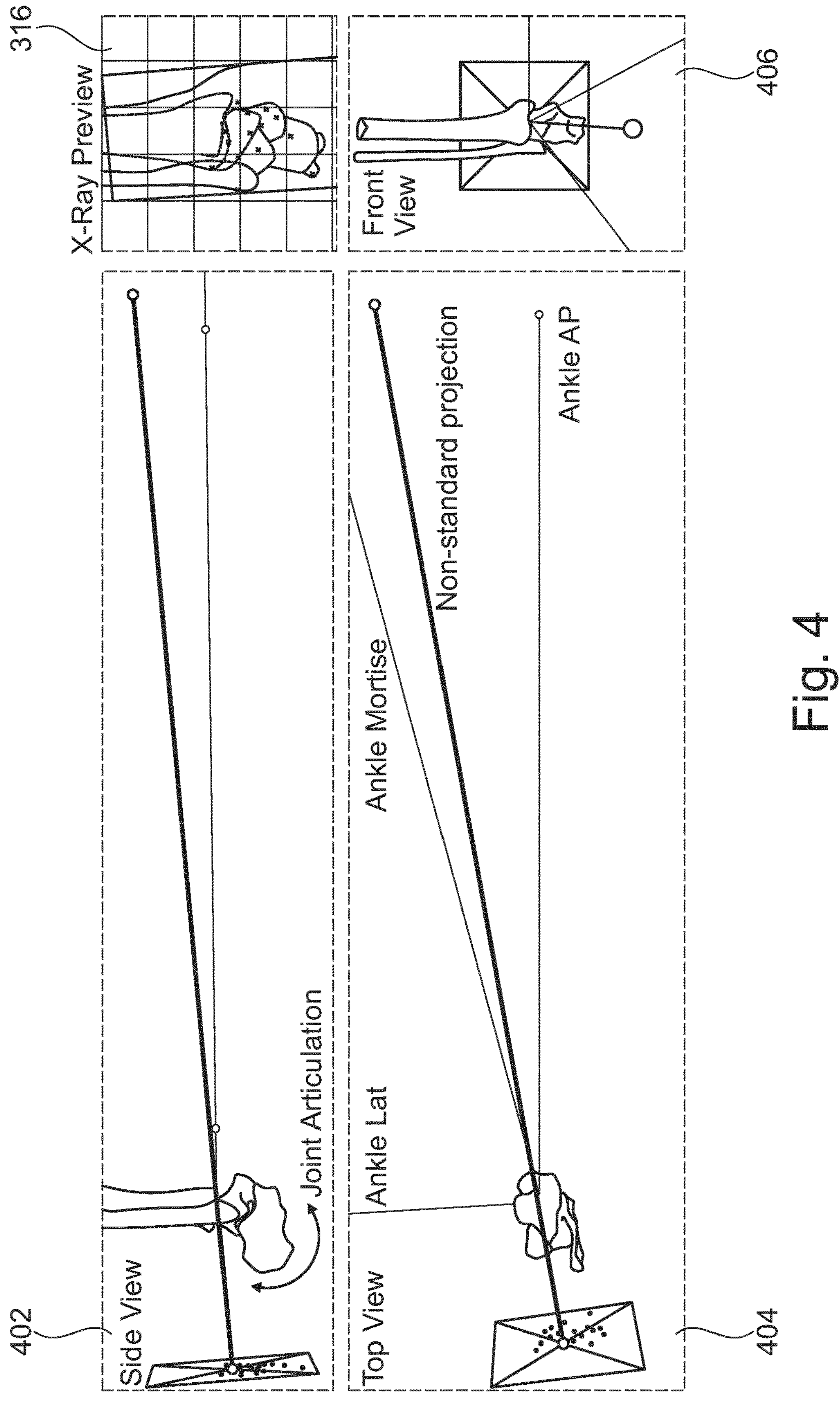
FIG. 4 illustrates a technical summary which is generated once the non-standard projection is specified.

FIG. 4 illustrates a technical summary which is generated once the non-standard projection is specified. The requested special projection may be summarized in terms of 2D projections in common anatomical planes. In this non-limiting example, the technical summary comprises a side view 402, a top view 404, and a front view 406 illustrating the non-standard projection, as well as the synthetic preview image 316.

Once the configuration is finalized, positional instructions for the radiographer are generated, e.g. by language processing or schematic image generation. These instructions enable the radiographer to achieve the non-standard projection. The positional instructions may provide the radiographer with recommendations on how to place the patient (e.g., supine, prone, and so on), on how to position support material (e.g., foam blocks), and/or on how to position the X-ray tube and detector.

Figure 5:
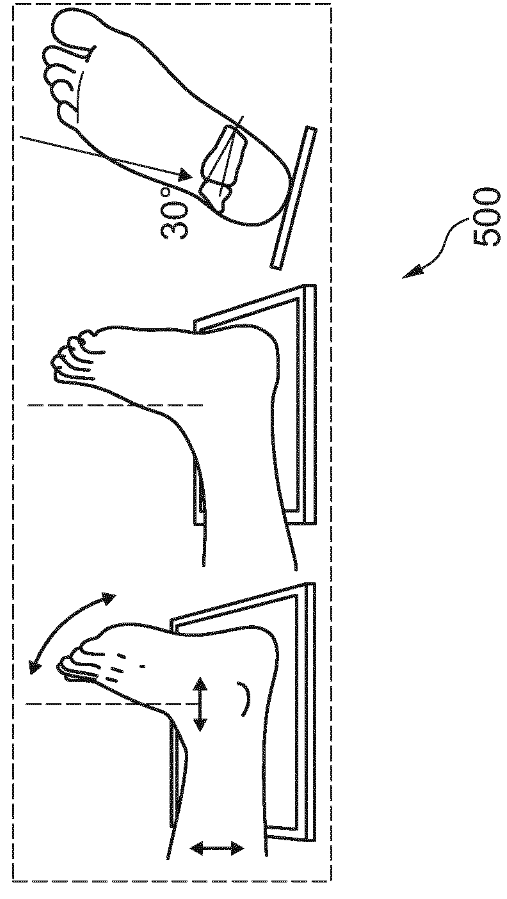
FIG. 5 illustrates positional instructions for the radiographer on how to achieve the non-standard projection.
Figure 5:
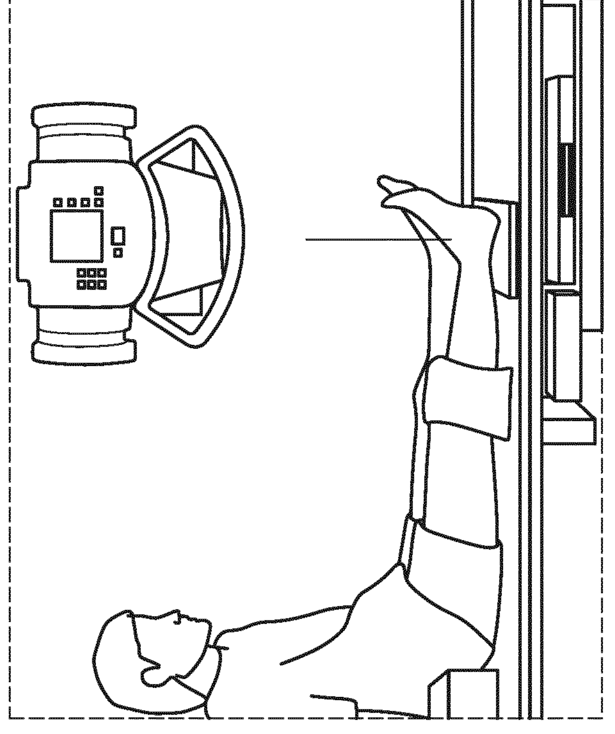

FIG. 5 illustrates one non-limiting example of positional instructions 500 for the radiographer on how to achieve the non-standard projection. The positional instructions can be generated by the planning tool 200 using a database that links the geometrical projection specifications to general guidance in medical language or via generative models, such as natural language processing (NLP). The positional instructions in this non-limiting example include graphical instructions on how to position the ankle joint in relation to the source and detector. In this example, the positional instructions comprise graphical instructions, in which the region of interest (in this case, an ankle) is represented both schematically and photographically. The positional instructions 500 comprise a schematic side view (left-hand image), a photographic side view (central image), and a schematic back view (right-hand image), with all three views depicting the ankle positioned on the detector. The dashed line represents the central beam emanating from the source. The two side views in this example instruct the radiographer to position the ankle in a target alignment with the ankle in the middle of the detector, which relates to a translatory instruction for the radiographer. The back view comprises an instruction to set a rotation angle with a value recommendation of 30° in relation to the radiation path. The orientation of the ankle is to turn over 30° in order to achieve the specified non-standard projection.

Suitable user interfaces and software, as well as standardized views and descriptions, may be used to communicate the positional instructions to other clinical stakeholders in the radiology value chain, for example the radiologist and other referring physician.

After the acquisition of the real X-ray image by the radiographer, an automatic review of the acquired image occurs. In one example, AI-based interpretation of the image data using a model of the anatomical joint of interest is used to highlight mismatching areas on the image which correspond to deviations from the requested special projection.

One example of such an AI-based interpretation technique is described in MAIRHÖFER, DOMINIK ET AL. An AI-based Framework for Diagnostic Quality Assessment of Ankle Radiographs. In Proceedings of the Fourth Conference on Medical Imaging with Deep Learning, no. 143, pp. 484-496, PMLR, 7-9 Jul. 2021. Based on clinical acceptance criteria, a request to perform a retake of the image may be suggested. In another example, by comparing image features (e.g., bone contours or landmarks) between the synthetic preview image and the actual acquired X-ray image, a similarity score can be computed using for example contour/landmark distances.

Additionally or alternatively, one or more pose estimation techniques can be used to derive pose parameters of the projection, which can be compared to the requested pose parameters to detect the deviation from the non-standard projection and indicate such as a positioning error. One example of a suitable pose estimation technique is described in S. KRÖNKE et al. CNN-based pose estimation for assessing quality of ankle-joint X-ray images. SPIE medical imaging conference. 2022. Paper 12032-37.

Numerous variations to the systems and methods described herein may be envisaged. For example, the planning tool 200 can be extended to check whether the requested non-standard projection is feasible using constraints imposed by the desired target X-ray system. The specified non-standard projection can be saved in the medical record of the patient (e.g., for use in re-examinations). If the patient has a complex record on a specific anatomy and a 3D reconstruction pre-exists (from CT or MR), a patient-specific 3D printed casting around the anatomy of interest can be generated and used to fixate the positioning of the joint. In particular, a proxy of the central beam (i.e. using a light gate or a laser) may be aligned with the casting in a unique way to fixate the pose, analogue to the leading lights used in marine navigation or the precision approach path indicator (PAPI) used in arial navigation. In one such example, the casting may comprise two or more openings that have be aligned in such a way that the proxy beam passes through them. In order to achieve this, the pose has to be fixed in a unique way. The openings are so positioned and orientated as to implement the specified non-standard projection.

Some smart radiology assistants comprise algorithms (e.g. "SmartOrtho") for automatically assessing the positioning quality of musculoskeletal X-ray exams. These algorithms measure 3D patient positioning parameters for a given image, whose values are compared against clinically-desired positioning parameters for a given exam type in order to assess the positioning quality. The planning tool 200 as described herein can be used as a graphical user interface for defining the desired optimal positioning for a given exam type (e.g. by the local head of radiology). Given this optimal positioning, the planning tool 200 might display the ray propagation and corresponding simulated X-ray image for deviating positioning (e.g. by first only rotating about the leg axis). The user, such an expert in radiology, may then indicate when the positioning quality becomes unacceptable. This user input can then be used to automatically configure the overall SmartOrtho algorithm to local preferences.

The methods and systems described herein may find application in the fields of digital X-ray, skeletal radiography, image quality, patient positioning, pose estimation, intuitive user interfaces, radiographer guidance.

Figure 6:
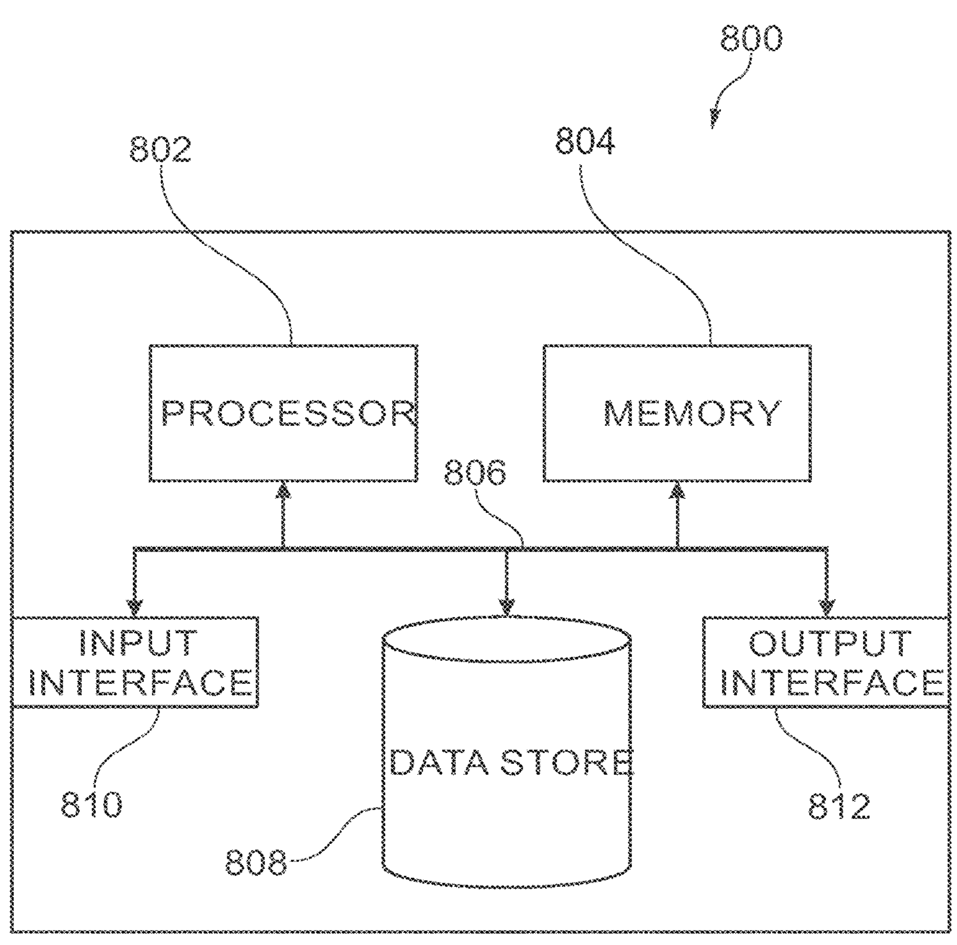
FIG. 6 illustrates a computing system that can be used in accordance with the systems and methods disclosed herein.

FIG. 6 illustrates an exemplary computing system 800 that can be used in accordance with the systems and methods disclosed herein. The computing system 800 may form part of or comprise any desktop, laptop, server, or cloud-based computing system. The computing system 800 includes at least one processor 802 that executes instructions that are stored in a memory 804. The instructions may be, for instance, instructions for implementing functionality described as being carried out by one or more components described herein or instructions for implementing one or more of the methods described herein. The processor 802 may access the memory 804 by way of a system bus 806. In addition to storing executable instructions, the memory 804 may also store conversational inputs, scores assigned to the conversational inputs, etc.

The computing system 800 additionally includes a data store 808 that is accessible by the processor 802 by way of the system bus 806. The data store 808 may include executable instructions, log data, etc. The computing system 800 also includes an input interface 810 that allows external devices to communicate with the computing system 800. For instance, the input interface 810 may be used to receive instructions from an external computer device, from a user, etc. The computing system 800 also includes an output interface 812 that interfaces the computing system 800 with one or more external devices. For example, the computing system 800 may display text, images, etc. by way of the output interface 812.

It is contemplated that the external devices that communicate with the computing system 800 via the input interface 810 and the output interface 812 can be included in an environment that provides substantially any type of user interface with which a user can interact. Examples of user interface types include graphical user interfaces, natural user interfaces, and so forth. For instance, a graphical user interface may accept input from a user employing input device(s) such as a keyboard, mouse, remote control, or the like and provide output on an output device such as a display. Further, a natural user interface may enable a user to interact with the computing system 800 in a manner free from constraints imposed by input device such as keyboards, mice, remote controls, and the like. Rather, a natural user interface can rely on speech recognition, touch and stylus recognition, gesture recognition both on screen and adjacent to the screen, air gestures, head and eye tracking, voice and speech, vision, touch, gestures, machine intelligence, and so forth.

Additionally, while illustrated as a single system, it is to be understood that the computing system 800 may be a distributed system. Thus, for instance, several devices may be in communication by way of a network connection and may collectively perform tasks described as being performed by the computing system 800.

Various functions described herein can be implemented in hardware, software, or any combination thereof. If implemented in software, the functions can be stored on or transmitted over as one or more instructions or code on a computer-readable medium. Computer-readable media include computer-readable storage media. Computer-readable storage media can be any available storage media that can be accessed by a computer. By way of example, and not limitation, such computer-readable storage media can comprise FLASH storage media, RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, include compact disc (CD), laser disc, optical disc, digital versatile disc (DVD), floppy disk, and Blu-ray disc (BD), where disks usually reproduce data magnetically and discs usually reproduce data optically with lasers. Further, a propagated signal is not included within the scope of computer-readable storage media. Computer-readable media also includes communication media including any medium that facilitates transfer of a computer program from one place to another. A connection, for instance, can be a communication medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio and microwave are included in the definition of communication medium. Combinations of the above should also be included within the scope of computer-readable media.

Alternatively, or in addition, the functionally described herein can be performed, at least in part, by one or more hardware logic components. For example, and without limitation, illustrative types of hardware logic components that can be used include Field-programmable Gate Arrays (FPGAs), Program-specific Integrated Circuits (ASICs), Program-specific Standard Products (ASSPs), System-on-a-chip systems (SOCs), Complex Programmable Logic Devices (CPLDs), etc.

It will be appreciated that the aforementioned circuitry may have other functions in addition to the mentioned functions, and that these functions may be performed by the same circuit.

The applicant hereby discloses in isolation each individual feature described herein and any combination of two or more such features, to the extent that such features or combinations are capable of being carried out based on the present specification as a whole in the light of the common general knowledge of a person skilled in the art, irrespective of whether such features or combinations of features solve any problems disclosed herein, and without limitation to the scope of the claims. The applicant indicates that aspects of the present invention may consist of any such individual feature or combination of features.

It has to be noted that embodiments of the invention are described with reference to different categories. In particular, some examples are described with reference to methods whereas others are described with reference to apparatus. However, a person skilled in the art will gather from the description that, unless otherwise notified, in addition to any combination of features belonging to one category, also any combination between features relating to different category is considered to be disclosed by this application. However, all features can be combined to provide synergetic effects that are more than the simple summation of the features.

While the invention has been illustrated and described in detail in the drawings and foregoing description, such illustration and description are to be considered exemplary and not restrictive. The invention is not limited to the disclosed embodiments. Other variations to the disclosed embodiments can be understood and effected by those skilled in the art, from a study of the drawings, the disclosure, and the appended claims.

The word "comprising" does not exclude other elements or steps.

The indefinite article "a" or "an" does not exclude a plurality. In addition, the articles "a" and "an" as used herein should generally be construed to mean "one or more" unless specified otherwise or clear from the context to be directed to a singular form.

A single processor or other unit may fulfil the functions of several items recited in the claims.

The mere fact that certain measures are recited in mutually different dependent claims does not indicate that a combination of these measures cannot be used advantageously.

A computer program may be stored/distributed on a suitable medium, such as an optical storage medium or a solid-state medium supplied together with or as part of other hardware, but may also be distributed in other forms, such as via the internet or other wired or wireless communications systems.

Any reference signs in the claims should not be construed as limiting the scope.

Unless specified otherwise, or clear from the context, the phrases "one or more of A, B and C", "at least one of A, B, and C", and "A, B and/or C" as used herein are intended to mean all possible permutations of one or more of the listed items. That is, the phrase "X comprises A and/or B" is satisfied by any of the following instances: X comprises A; X comprises B; or X comprises both A and B.

The term "module" as used herein may be replaced by "system", "circuitry", "tool" according to the specific implementation.

The invention claimed is:

1. A computer-implemented method to be used in radiology workflow, the method comprising:

enabling a first user to prepare an imaging examination request defining a non-standard projection for a radiographic image;

processing the imaging examination request to generate positional instructions on how to achieve the non-standard projection, outputting the positional instructions to a second user, and receiving a radiographic image acquired using the non-standard projection; and determining whether the received radiographic image fulfils the imaging examination request.

2. The method of claim 1, wherein determining whether the received radiographic image fulfils the imaging examination request comprises calculating one or more similarity metrics describing similarity between the received image and a reference image.

3. The method of claim 2, wherein the reference image is a synthetic preview image generated during the planning step.

4. The method of claim 1, wherein determining whether the received radiographic image fulfils the imaging examination request comprises deriving pose parameters of the projection used in the received image, and comparing the derived pose parameters to requested pose parameters.

5. The method of claim 1, wherein determining whether the received radiographic image fulfils the imaging examination request comprises obtaining an AI-based interpretation of the received image highlighting mismatched areas in the received image.

6. The method of claim 1, comprising enable the imaging examination request to be prepared via a user interface which presents a 3D model of the anatomy to be imaged, wherein the 3D model enables pose manipulations for one or more of the anatomy of interest, detector, and source.

7. The method of claim 6, wherein the 3D model comprises an articulated joint model which enables an indication of the flexion of the joint to be specified.

8. The method of claim 6, wherein the user interface indicates the non-standard projection relative to one or more standard projections.

9. The method of claim 6, wherein the user interface enables a synthetic preview radiographic image to be shown.

10. The method of claim 1, wherein the positional instructions comprise graphical instructions comprising schematic representations of one or more of the anatomy of interest, detector, and source.

11. The method of claim 10, wherein the graphical instructions are animated to indicate how one or more of the anatomy of interest, detector, and source should be moved to achieve the non-standard projection.

12. The method of claim 1, wherein the positional instructions comprise textual instructions or audio instructions generated using natural language processing.

13. The method of claim 1, wherein outputting the positional instructions comprises producing a patient-specific casting for surrounding the anatomy of interest, wherein the casting is configured to provide one or more visual indications of the non-standard projection.

14. A computing system configured to perform the method of claim 1.

15. A non-transitory computer-readable medium comprising instructions which, when executed by a computing system, cause the computing system to perform the method of claim 1.

* * * * *